(12) United States Patent
Van Hoorn

(10) Patent No.: US 7,241,369 B2
(45) Date of Patent: Jul. 10, 2007

(54) ELECTROCHEMICAL SENSOR

(75) Inventor: Hendrik Van Hoorn, Zevenhuizen (NL)

(73) Assignee: Mettler-Toledo AG, Greifensee (CH)

( * ) Notice: Subject to any disclaimer, the term of this patent is extended or adjusted under 35 U.S.C. 154(b) by 814 days.

(21) Appl. No.: 10/655,038

(22) Filed: Sep. 5, 2003

(65) Prior Publication Data
US 2005/0072672 A1 Apr. 7, 2005

(30) Foreign Application Priority Data
Sep. 6, 2002 (DE) ............... 102 41 779

(51) Int. Cl.
*G01N 27/333* (2006.01)
*H01L 23/58* (2006.01)
(52) U.S. Cl. ..................... 204/416; 257/253
(58) Field of Classification Search ............... 257/253; 204/416–418, 403.01–403.15, 433, 435
See application file for complete search history.

(56) References Cited

U.S. PATENT DOCUMENTS

| | | | |
|---|---|---|---|
| 4,505,799 A * | 3/1985 | Baxter | 204/416 |
| 6,117,292 A | 9/2000 | Ahmad | |
| 6,153,070 A | 11/2000 | Maurer et al. | |

FOREIGN PATENT DOCUMENTS

| | | |
|---|---|---|
| DE | 31 16 884 A1 | 1/1982 |
| DE | 41 15 399 C1 | 7/1992 |
| EP | 0 063 213 | 10/1982 |
| EP | 0467479 A1 * | 7/1991 |
| EP | 691 22 999 T2 | 3/1997 |
| NL | 1003458 | 1/1998 |

OTHER PUBLICATIONS

Derwent abstract of NL 1003458 C2, issued Jan. 7, 1998.*

* cited by examiner

*Primary Examiner*—Alex Noguerola
(74) *Attorney, Agent, or Firm*—Buchanan Ingersoll & Rooney PC

(57) ABSTRACT

An electrochemical sensor has a sensor housing and an ion-sensitive field effect transistor (ISFET) with a source connection (S) and a drain connection (D). An ion-sensitive surface area (IS) on the front surface of the ISFET is immersible in a measuring medium. A clamping element serves to clamp the ISFET with its rear surface against an end surface of the sensor housing. The clamping element has a central opening leaving the ion-sensitive surface area (IS) exposed. A leak-tight circular connection between the clamping element and the sensor housing is formed by vibratory, preferably ultrasonic, welding. The ISFET is sandwiched between two rubber-elastic elements, at least one of which forms a leak-tight seal against penetration of the measuring medium from the ion-sensitive surface area (IS) to the source- and drain connections (S) and (D).

15 Claims, 3 Drawing Sheets

ELECTROCHEMICAL SENSOR

CROSS-REFERENCE TO RELATED APPLICATIONS

This application claims priority under 35 U.S.C. §119 to German Application No. 10241779.2 filed in Germany on 6 Sep. 2002, the entire contents of which are incorporated herein by reference.

BACKGROUND

Among the widely used electrochemical sensors with a sensor element and/or sensor housing consisting of glass, so-called non-glass sensors are gaining in importance. An application for non-glass sensors is for example the measurement of concentrations in production processes in the food industry. In particular the measurement of pH values that were previously measured primarily with glass electrodes is or will become outlawed in many industrial situations. The purpose of the new legislation is to avoid the dangers associated with a possible breakage of glass parts, e.g., in a production chain in the food industry.

The design of a glass-free electrochemical sensor poses on the one hand a problem that instead of a sensor housing made of glass, an enclosure of a different material is to be selected. As a solution, there are a variety of suitable polymer materials available. The material should meet application-specific requirements, i.e., adequate mechanical stability and chemical resistance, and it should be a good electrical insulator. On the other hand, there is a problem of finding a glass-free alternative for the sensor membrane, in particular for pH-sensors which usually contain a membrane of pH glass as a essential component of the measuring system. This makes it appropriate to use a different measuring principle.

To provide glass-free ion-sensitive elements that can in particular be configured as glass-free pH-sensitive elements, ion-sensitive field effect transistors, hereinafter referred to by the customary acronym ISFET, present themselves as a solution. For example, a method and a circuit for measuring ion activity in liquids involving the use of an ISFET are described in DE 3116884 A1. The ISFET in this case contains an insulating layer acting as transistor gate. The insulating layer, which has the function of an ion-sensitive surface area, is arranged between a source electrode and a drain electrode. A pH-measuring device with an electrode including an ISFET is described, e.g., in EP 63213 B1.

The aforementioned documents give only a schematic indication of the arrangement of the ISFET in the sensor. However, when attempting to implement this concept in practice, it becomes evident that the positioning, mounting and the electrical connections of the ISFET are of importance for a functional sensor. As a ground rule, it should be ensured that certain parts of the sensor are sealed tightly against leaks and moreover that the ISFET is protected against excessive mechanical stress, e.g., in applications involving increased pressure.

Sensors which belong generically to the same type are presented in U.S. Pat. No. 6,117,292 and U.S. Pat. No. 6,153,070. They have a sensor housing containing an ISFET in the shape of a small disc. A source connection and a drain connection are arranged on the rear side of the disc. At the front side, the disc has an ion-sensitive surface area for immersion into a measuring medium. The sensors have a stacked configuration in which the ISFET is clamped against a plate-shaped base that serves as a mechanical seat and at the same time as a lead-off element. The latter function is achieved through a design with direction-specific electrical conductivity due to a laminated structure of the plate-shaped base with alternating insulating- and conducting layers running substantially perpendicular to the main plane of the plate-shaped base. As a result, the base is electrically conductive in the direction perpendicular to its main plane and at the same time electrically insulating in one direction of the main plane. This arrangement provides the electrical connections to the source- and drain contacts on the rear side of the ISFET. Drawbacks of these sensors lie in their complexity and high manufacturing cost. In addition, the desire to arrange the source- and drain connections on the rear side of the ISFET represents a particular disadvantage, because it does not conform to the customary design of ISFETs and thus adds to the cost and limits the selection of available types of ISFETs.

A reference electrode is described in NL 1003458 C, which instead of the customary Ag/AgCl half cell with glass frit and conductive gel uses an Ag platelet coated with an AgCl film, with a thin $SiO_2$ film arranged on top of the AgCl film. A clamping element serves to clamp the Ag platelet against an end surface of a sensor housing, so that the rear surface of the platelet, which faces away from the AgCl-coated side bears against the end surface of the sensor housing. The clamping element has a central opening leaving a mid-portion of the AgCl film exposed. A substantially ring-shaped sealing element is arranged between the clamping element and the AgCl platelet, surrounding the mid-portion of the AgCl as a tight seal against leakage of the measuring medium. It is mentioned in NL 1003458 C that the clamping element (referred to in Dutch as "kopdeel", meaning "head part") is attached to the sensor housing (referred to as "huls", meaning "casing") by means of an adhesive bond, but preferably by ultrasonic welding. However, this reference gives no indication regarding the spatial arrangement of the ultrasonic welding bond and in particular whether it forms a leak-tight seal running in a closed circle. There is furthermore no indication on how to perform the welding procedure. The ultrasonic welding process as well as other kinds of vibratory welding present a problem that in addition to the components to be bonded together, adjacent components are also subjected to some degree of vibration. This may be tolerable in the case of the Ag platelet of the aforementioned reference. However, if an ISFET were to be installed instead of the Ag platelet, the vibrations reaching the ISFET would cause cracks or separation of the film layer. Furthermore, the wire bonds of the lead-off wires to the source- and drain contacts of some types of ISFETs are particularly prone to getting damaged by vibrations. These kinds of problems do not exist in the reference electrode described in NL 1003458 C and accordingly this reference offers no suggestion whatsoever for a solution. Furthermore, the arrangement described in NL 1003458 C is designed with electrical contacts arranged on the rear side, analogous to the arrangements of U.S. Pat. No. 6,117,292 and U.S. Pat. No. 6,153,070, and is therefore not suitable for the particularly common type of ISFETs with electrical leads on the front side.

SUMMARY

An improved electrochemical sensor is disclosed.

A sensor is disclosed that has a sensor housing and an ion-sensitive field effect transistor (ISFET) with a source connection and a drain connection. An ion-sensitive surface area arranged on a frontal surface of the ISFET can be designed for immersion in a measuring medium. A clamping element serves to clamp the ISFET against an end surface of a sensor housing, so that the rear surface of the ISFET which faces away from the ion-sensitive surface area bears against the end surface of the sensor housing. The clamping element has a central opening leaving a mid-portion of the ion-sensitive surface area of the ISFET exposed, while the source connection and the drain connection are arranged in an internal part of the sensor that is protected from penetration by the measuring medium. The clamping element has a vibration-welded (for example, ultrasound-welded), leak-tight circular connection with the sensor housing, which ensures a durable and reliable mechanical connection between the clamping element and the sensor housing and is comparatively easy to produce. The welded circular connection prevents the penetration of measuring medium between the clamping element and the sensor housing and thereby ensures that no contact occurs between the measuring medium and the source contact or the drain contact. Because of the sandwiched seating of the ISFET between two rubber-elastic elements, no vibrations are transmitted from the sensor housing to the ISFET, which prevents the problem of undesirable mechanical stress and damage to the ISFET in the process of making the circular connection by means of vibration- or ultrasound welding. Due to the fact that at least one of the rubber-elastic elements forms a leak-tight seal between the ion-sensitive surface area on one side and the connections of the source and drain on the other side, the advantages of a compact design configuration and an uncomplicated and cost-effective production of the sensor can be achieved. Exemplary embodiments are suitable not only for ISFETs with electrical contacts on the rear side, but also for the particularly common type of ISFETs with electrical leads on the front side.

An exemplary sensor can be used for configurations where the electrical leads are arranged at the front side, at the back side, and in some cases on the edge of the ISFET. According to an exemplary embodiment, the source connection and the drain connection are arranged on the front side of the ISFET.

The rubber-elastic element can in principle have a plurality of different shapes. However, according to an exemplary embodiment, at least the rubber-elastic element that performs a sealing function is configured as a ring seal.

In an exemplary embodiment, the sensor housing has a channel that ends at a central opening in the front surface of the housing. The opening is located entirely on the opposite side of the leak-proof seal in relation to the measuring medium.

In a further developed version of this embodiment, the channel is filled with a potting compound that extends up to the backside of the ISFET and provides a mechanical support for the ISFET. This concept is advantageous for sensors that are used for pressurized media.

The sensor according to any of the preceding embodiments can be designed with a tubular shape. A tubular design is advantageous for single-rod sensor probes.

For many applications, a cylindrically symmetric sensor configuration suggests itself, in which the ISFET is oriented substantially at a right angle relative to a longitudinal axis of the sensor housing. However, in certain embodiments the ion-sensitive surface area of the ISFET is arranged at an oblique angle relative to the longitudinal axis of the sensor housing. This concept allows a hydrodynamically optimized orientation of the ion-sensitive surface area of the sensor for measurements in a moving stream of a measuring medium. The arrangement at an oblique angle is furthermore particularly advantageous for installations where the sensor is lowered into place from vertically above, because it avoids the problem that rising gas bubbles could get caught and form an undesirable gas pocket on the ISFET.

According to an advantageous embodiment, the sensor is equipped with a temperature gauge to allow a correction of the measurement values based on the local temperature at the ISFET.

It is possible at least in principle to configure ISFETs as ion-specific sensor elements for the most divers species of ions. As an exemplary embodiment, the ISFET is designed as a pH-sensitive element.

The sensor can be used in combination with any kind of external reference electrode. According to an exemplary embodiment, the sensor can be equipped with a reference electrode, which leads to a compact and easy-to-use single-rod configuration.

BRIEF DESCRIPTION OF THE DRAWINGS

The following detailed description of preferred embodiments refers to the attached drawings, wherein.

DETAILED DESCRIPTION OF PREFERRED EMBODIMENTS

Figure 1:
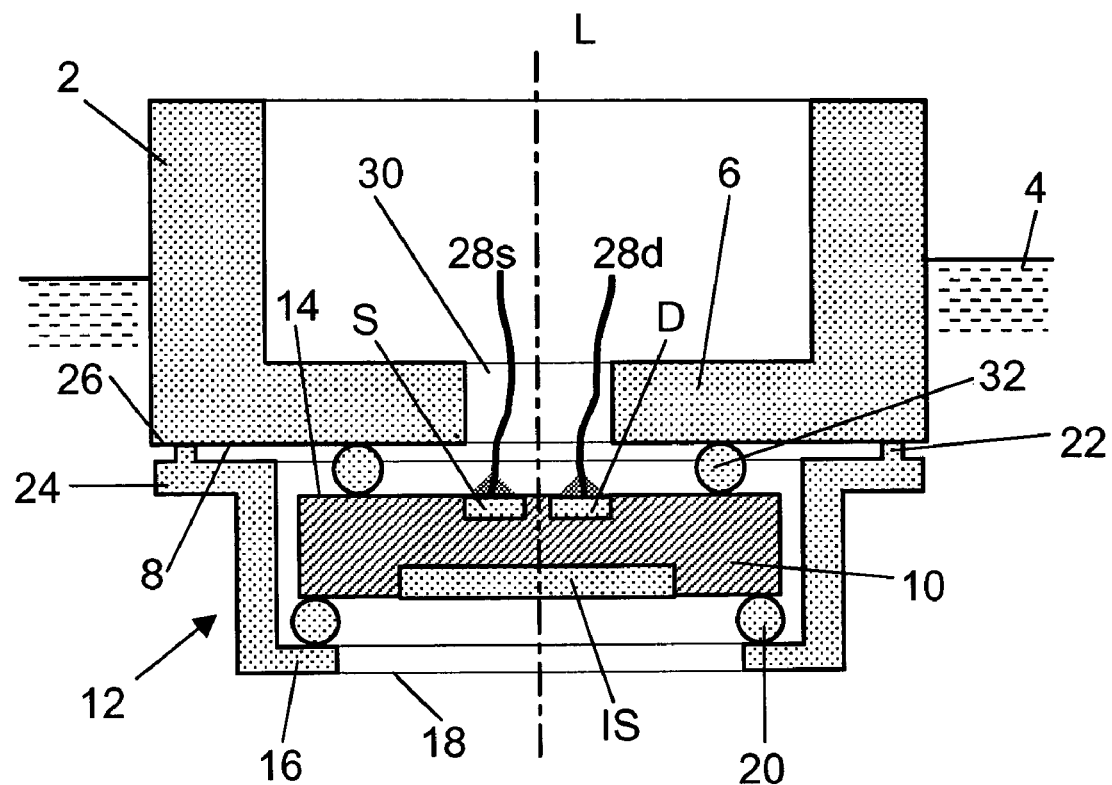
FIG. 1 represents an exemplary electrochemical sensor in a lengthwise sectional view.

The sensor shown in FIG. 1 has a substantially cylindrical sensor housing 2 of polyether ether ketone (PEEK), which is immersed in a measuring medium 4. The sensor housing 2 has a bottom wall 6 with an external end surface 8. The sensor is equipped with a disc-shaped ion-sensitive field effect transistor (ISFET) 10 which has a source connection S and a drain connection D on its backside and an ion-sensitive surface area IS in contact with the measuring medium on the front side. A sleeve-shaped clamping element 12 of the same material as the sensor housing pushes the ISFET 10 against the end surface 8 of the sensor housing 2, so that the rear surface 14 of the ISFET which faces away from the ion-sensitive surface area IS is clamped against the end surface 8 of the sensor housing 2. To perform this function, the clamping element 12 has an inward-projecting flange collar 16 on the side that faces away from the sensor housing 2. The flange collar 16 overlaps the periphery of the ISFET 10, while a central opening 18 of the clamping element 12 leaves the ion-sensitive surface area IS exposed. A first rubber-elastic element 20, e.g., of ethylene propylene diene terpolymer (EPDM) or in some cases of a fluoro-elastomer such as Viton®, is arranged between the flange collar 16 and the ISFET 10. In the illustrated example, the first rubber-elastic element 20 consists of a seal ring, so that it simultaneously forms a leak-tight barrier surrounding the ion-sensitive surface area IS and closing off the source connection S and the drain connection D. In other words, the ion-sensitive surface area on the one hand and the source- and drain connections on the other hand are located on opposite sides of the leak-tight barrier formed by the seal ring 20.

The clamping element 12 is connected to the sensor housing 2 through a circular bond 22 produced by ultrasound welding. The circular bond 22 in the illustrated example lies between an outward-projecting flange collar 24 of the clamping element 12 and a ring-shaped border zone 26 of the end surface 8 of the sensor housing 2. As can further be seen in FIG. 1, the seal ring 20 and the circular bond 22 prevent the measuring medium 4 from making contact with the source connection S and the drain connection D. Thus, the measuring medium cannot enter into the interior part of the sensor where the connections S and D are located.

The source connection S and drain connection D are connected, respectively, to the lead-off wires 28s and 28d that lead through an opening 30 of the bottom wall 6 to a measuring instrument that is not shown in the drawing.

A second rubber-elastic element 32 is arranged between the rear surface 14 of the ISFET 10 and the end surface 8 of the sensor housing 2, so that the ISFET is sandwiched between the two rubber-elastic elements 20 and 32. This arrangement prevents to a large extent that vibrations are transmitted from the sensor housing 2 or from the clamping element 12 to the ISFET 10. This is of particular importance in the assembly process of the sensor, i.e., in forming the circular bond 22 by means of ultrasound welding or another suitable kind of vibration welding. This welding process for joining the clamping element 12 and the sensor housing 2 subjects at least the components adjacent to the weld to a high-frequency vibration, and if the vibration is allowed to propagate to the ISFET 10, the latter can easily get damaged.

In the example illustrated in FIG. 1, the source connection S as well as the drain connection D are arranged in a central area of the rear surface 14 of the ISFET 10. For the sealing of the sensor it is therefore unimportant which of the two rubber-elastic elements forms the leak-tight barrier. It is in particular possible to use two identical ring seals, e.g., two round-profiled rings of the same material and possibly with the same dimensions.

Figure 2:
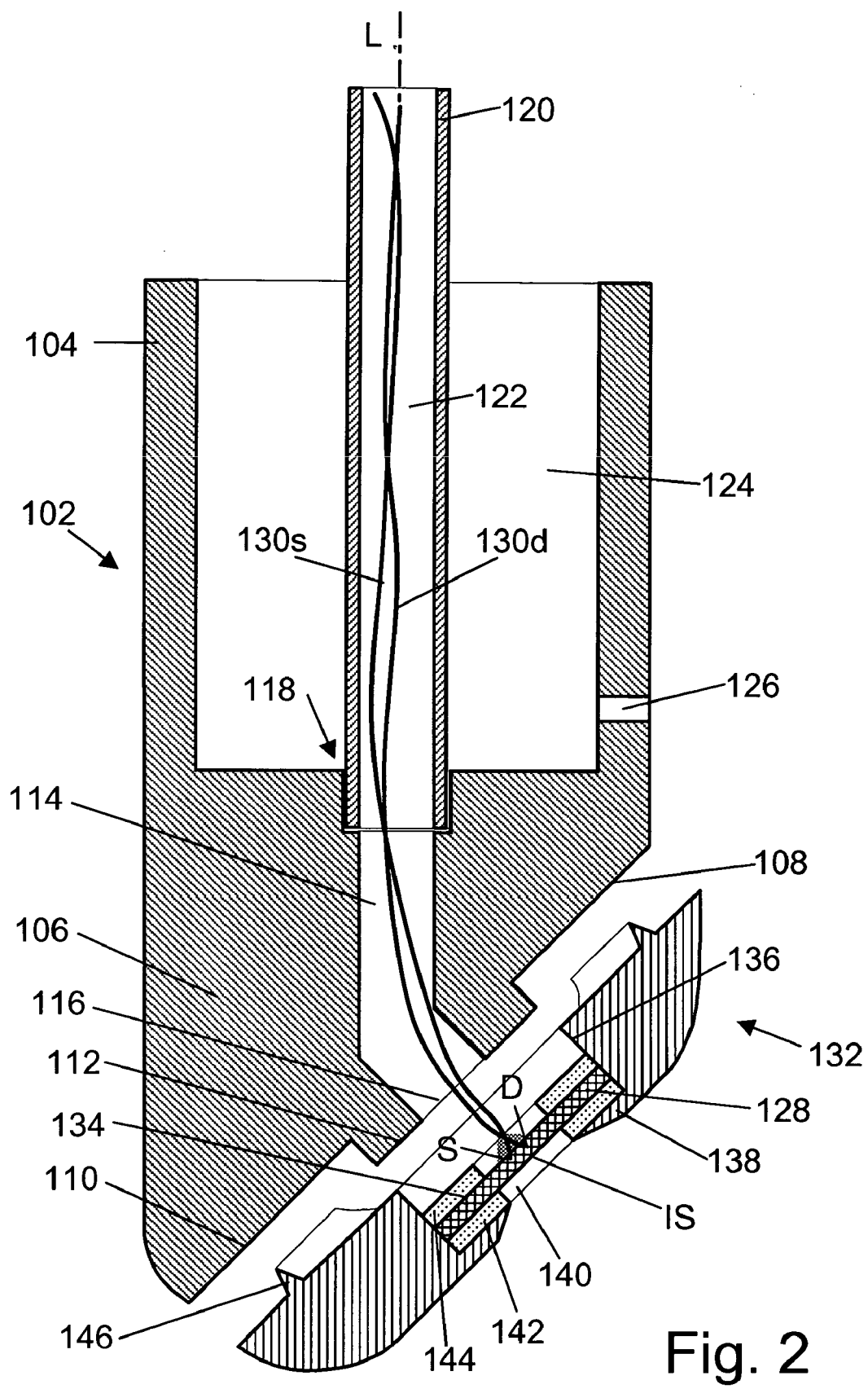
FIG. 2 represents a lengthwise sectional view of a further exemplary electrochemical sensor prior to final assembly.

FIG. 2 illustrates a further sensor in a state prior to final assembly. The sensor includes a sensor housing 102, for example of polyether ether ketone (PEEK) with a tubular sensor shaft 104 and a bottom section 106 terminating in an external end surface 108. The end surface 108 is positioned at an oblique angle relative to the longitudinal axis L of the sensor shaft 104, e.g., inclined at an angle of 45°, and has a ring-shaped border zone 110 as well as a likewise ring-shaped core zone 112 that protrudes from the border zone 110. The bottom section 106 has a central channel 114 that ends on one side in a frontal opening 116 of the core zone 112 and on the other side in an internal opening 118 of the bottom section 106. An interior tube 120 which may, e.g., consist likewise of PEEK, is inserted into the internal opening 118 with a leak-tight fit. The interior tube encloses an interior sensor compartment 122 also defines an intermediate sensor compartment 124 between the outside of the tube 120 and the inside of the sensor shaft 104. The intermediate sensor compartment 124 is intended in particular to hold a reference electrode. A diaphragm can be seated in a known manner in a passage hole 126 in the sensor shaft 104.

The sensor further includes a disc-shaped ISFET 128 with a source connection S and a drain connection D at its backside, to which the respective lead-off wires 130s and 130d are attached. The front side of the ISFET has an ion-sensitive surface area IS for immersion into a measuring medium. The lead-off wires 130s and 130d are routed through the frontal opening 116, the central channel 114 and the interior tube 120, terminating in an indicator device (not shown in the drawing).

A clamping element 132 made of the same material as the sensor housing serves to press the ISFET 128 with its backside 134 against the end surface 108 of the sensor housing 102. The clamping element 132 has a central recess 136 on the side which (in the assembled condition) faces the end surface 108 of the sensor housing 102. The central recess 136, which is wider than the diameter of the projecting core zone 112, serves to receive the ISFET 128 which is seated against an inward-projecting flange collar 138 of the central recess 136. The flange collar 138 surrounds a central opening 140 of the clamping element 132, leaving the ion-sensitive surface area IS exposed.

As shown in FIG. 2, the ISFET 128 is sandwiched between a first rubber-elastic element 142 and a second rubber-elastic element 144. Both of the rubber-elastic elements are in the shape of flat rings and consist for example of a fluoro-elastomer. It is advantageous if the outside diameter of the rubber-elastic elements 142 and 144 is substantially equal to the internal diameter of the central recess 136, and if the internal diameter of the central recess 136 is only slightly larger than the outside diameter of the protruding core zone 112 for a firm fit between the different components, except that the outside edge of the ISFET 128 should not sit firmly against the wall of the central recess 136 in order to prevent undesirable vibrations from reaching the ISFET 128 during the ultrasound welding process.

The clamping element 132 has a sharp circular ridge 146 protruding on the side that faces the sensor housing and surrounding the central recess 136. The circular ridge 146 is designed to direct the energy to form a weld seam with the sensor housing 102. As an arrangement that is known per se, a peripheral area 110 of the end surface 108 can have a circular groove designed to receive the ridge 146 to serve as a positioning aid in the assembly of the sensor. As an alternative, the ridge could be on the end surface 108 and the groove on the clamping element 132.

After the sandwiched arrangement of the ISFET 128 and the two rubber-elastic elements has been seated in the central recess 136 of the clamping element 132 (as shown in FIG. 2), the assembly of the sensor continues as follows: First, the clamping element 132 is placed against the end surface 108 by seating the central recess 136 on the projecting core zone 112. This brings the sharp ridge 146 into contact with the border zone 110 of the sensor housing 102. Next, an ultrasonic welding operation is performed by applying ultrasound to the immediate vicinity of the sharp ridge 146. This causes a localized melting along a circle where the ridge 146 contacts the border zone 110, which produces a weld seam that forms a leak-tight barrier against the measuring medium.

The first purpose of the two rubber-elastic elements 142 and 144 is as a protective cushion to keep vibrations away from the ISFET 128 that is sandwiched between them. In addition, at least one of the rubber-elastic elements serves as a leak-tight closure element of the sensor. The seal element therefore needs to be under a certain amount of clamping pressure in the assembled state, i.e., after the ultrasound welding has been completed. This purpose is met in particular through an appropriate choice of the thickness of the two rubber-elastic elements 142 and 144, if the dimensions of the other components are given. However, to choose the correct thickness, it is necessary to know in advance the thickness of the weld seam that is formed in the ultrasound welding process. In practice, the seam thickness can be determined through ultrasonic welding experiments using different parameter settings.

Before or after the ultrasonic welding operation, the interior tube 120 is inserted into the internal opening 118 of the bottom section 106 and connected to the rim of the internal opening through a leak-tight bond, e.g., by means of an epoxy adhesive.

In certain applications of the sensor, the pressure of the measuring medium exceeds the pressure in the interior sensor space. This causes a pressure load on the ISFET which can cause a measuring error. To avoid this problem, it is practical to back up the ISFET with a mechanical support. However, as the mechanical support would transmit vibrations during the ultrasound welding, it cannot be put in place until after the ultrasonic welding process has been completed. This is accomplished advantageously by filling the interior sensor compartment from the end of the interior tube with an epoxy compound up to the rear surface 134 of the ISFET 128. After hardening, the epoxy compound serves as a mechanical support. This concept is illustrated in the context of the following embodiment.

Figure 3:
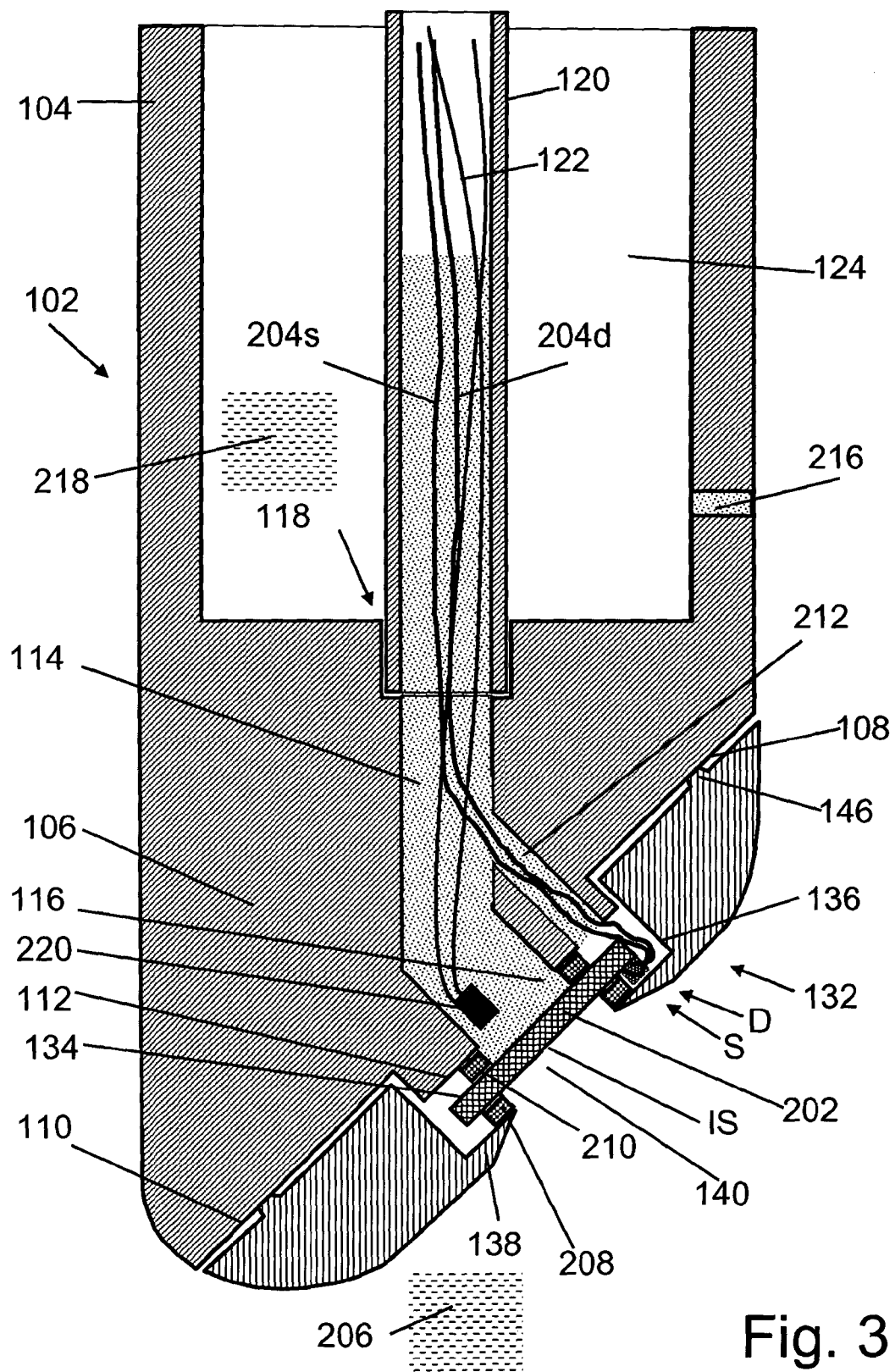
FIG. 3 represents a further exemplary electrochemical sensor in a lengthwise sectional view.

The embodiment shown in FIG. 3 represents a further configuration of a sensor in an assembled state. The sensor of FIG. 3 is largely identical with the sensor of FIG. 2. Accordingly, elements in FIG. 3 that are analogous to FIG. 2 are identified by the same reference symbols and their description will not be repeated. In contrast to the preceding example, the source connection S and the drain connection D are arranged on the front side rather than on the backside of the ISFET 202, more specifically in a border area of the front surface. The lead-off wires 204s and 204d are therefore connected at the front side of the ISFET 202. The ion-sensitive surface area IS is located on the front side as in the preceding embodiments and is shown immersed in a measuring medium 206. The ISFET 202 is sandwiched between an outer, first rubber-elastic element 202 and an inner, second rubber-elastic element 210. Both of the rubber-elastic elements are flat rings of an elastomeric material. The outside diameter of the rubber-elastic elements 208 and 210 is smaller than the internal diameter of the central recess 136 of the clamping element 132 in order to leave space for the passage of the lead-off wires 204s and 204d.

The bottom section 106 has a lateral channel 212 running on the side of the central channel 114. The lateral channel 212 runs between a peripheral area of the core zone 112 and the interior sensor compartment 122, leading for example into the central channel 114 as shown in the example of FIG. 3. The lateral channel 212 serves as a passage for the lead-off wires 204s and 204d, so that the lead-off wires are kept clear of the second rubber-elastic element 210.

As will be understood directly from FIG. 3, in order to arrange the lead-off wires 204s and 204d along the side, it is necessary for the outer, first rubber-elastic element 208 to function as a leak-tight barrier against the measuring medium 206.

As has already been described in the context of the sensor of FIG. 2, the interior sensor space is filled with a potting compound 214, for example an epoxy resin material, from the interior tube 120 through the central channel 114 as well as through the lateral channel up to the back surface 134 of the ISFET 202.

The sensor of FIG. 3 is configured as a single-rod measuring chain, for example for measuring pH values. In this case, the ISFET 202 is configured as a pH-sensitive element, and the intermediate sensor compartment 124 contains a reference electrode, for example an Ag/AgCl electrode (not shown in the drawing). The lateral passage hole 126 in the sensor shaft 104 contains a diaphragm 216, for example a ceramic diaphragm, which provides the electrical contact between the measuring medium 206 and the reference electrolyte 218 in the intermediate sensor compartment 124.

The sensor of FIG. 3 is further equipped with a temperature sensor 220, for example a platinum resistor, which is imbedded in the potting compound 214 in the area of the frontal opening 116. It serves to monitor the temperature at the ISFET and to apply a temperature correction to the measurement values if necessary.

The orientation of the end surface of the housing, and thus also of the ISFET, at an angle of about 45° relative to the longitudinal axis L (see FIG. 2) and the rounded contour portions in the embodiments of FIGS. 2 and 3 contribute to preventing undesirable turbulence and other hydrodynamic disturbances when measurements are performed in a moving stream of a measuring medium. If the sensor is installed in a vertical position, the arrangement of the ISFET at an oblique angle further avoids the problem that rising gas bubbles could accumulate and form an undesirable gas pocket in the ion-sensitive area.

The sensors of the foregoing description are distinguished by the fact that they can, for example, be sterilized by a direct treatment with hot water or steam without suffering damage. As a further advantage, the parts of the sensor that can come into contact with the measuring medium can be free of any adhesive bonding connections. This can avoid on the one hand a decomposition of the adhesive caused by the measuring medium, and on the other hand it can make the sensor suitable for use with food products, beverages and the like, because there is no possibility of a toxic adhesive component coming into contact with the measuring medium.

The embodiments described herein are intended to serve only as examples for the shape, configuration, materials and dimensions. Depending on the requirements of an application, those who are skilled in the will be able to find modified versions that are based on the same principles.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within.

What is claimed is:

1. An electrochemical sensor, comprising
   a sensor housing;
   an ion-sensitive field effect transistor (ISFET) with a source connection (S), a drain connection (D), a front surface having an ion-sensitive surface area (IS) that is immersible in a measuring medium, and a rear surface facing away from the ion-sensitive surface area;
   a clamping element to clamp the ISFET with the rear surface against an end surface of the sensor housing, said clamping element having a central opening leaving the ion-sensitive surface area (IS) exposed; and
   a first rubber-elastic element placed against said front surface and a second rubber-elastic element placed against the rear surface, so that the ISFET is sandwiched between the first and second rubber-elastic elements;
   wherein the source connection (S) and the drain connection (D) are arranged in an interior space of the electrochemical sensor; wherein the clamping element has a leak-tight circular connection to the sensor housing formed by vibratory welding; and wherein at least one of said first and second rubber-elastic elements forms a leak-tight seal against penetration of the measuring medium from the ion-sensitive surface area (IS) to said source- and drain connections (S) and (D).

2. The electrochemical sensor of claim 1, wherein the source connection (S) and the drain connection (D) are arranged on said front surface.

3. The electrochemical sensor of claim 2, wherein at least one of the first and second rubber-elastic elements is configured as a ring seal.

4. The electrochemical sensor of claim 3, wherein the sensor housing has a channel ending in a frontal opening of the end surface, and wherein the entire frontal opening and the measuring medium are located, respectively, on opposite sides of the leak-tight circular connection.

5. The electrochemical sensor of claim 4, wherein the channel is filled with a potting compound which extends up to the rear surface and forms a mechanical support for the ISFET.

6. The electrochemical sensor of claim 4, wherein the sensor housing is of a substantially tubular shape.

7. The electrochemical sensor of claim 4, wherein the ion-sensitive surface area (IS) is oriented at an oblique angle relative to a longitudinal axis (L) of the sensor housing.

8. The electrochemical sensor of claim 1, wherein at least one of the first and second rubber-elastic elements is configured as a ring seal.

9. The electrochemical sensor of claim 1, wherein the sensor housing has a channel ending in a frontal opening of the end surface, and wherein the entire frontal opening and the measuring medium are located, respectively, on opposite sides of the leak-tight circular connection.

10. The electrochemical sensor of claim 9, wherein the channel is filled with a potting compound which extends up to the rear surface and forms a mechanical support for the ISFET.

11. The electrochemical sensor of claim 1, wherein the sensor housing is of a substantially tubular shape.

12. The electrochemical sensor of claim 11, wherein the ion-sensitive surface area (IS) is oriented at an oblique angle relative to a longitudinal axis (L) of the sensor housing.

13. The electrochemical sensor of claim 1, comprising:
a temperature sensor for measuring a temperature of the ISFET.

14. The electrochemical sensor of claim 1, wherein the ISFET is configured as a pH-sensitive element.

15. The electrochemical sensor of claim 1, comprising:
a reference electrode.

* * * * *